US011642035B2

(12) United States Patent
Ziegler et al.

(10) Patent No.: US 11,642,035 B2
(45) Date of Patent: May 9, 2023

(54) HEART RATE RECOVERY ASSESSMENT

(71) Applicant: Medtronic, Inc., Minneapolis, MN (US)

(72) Inventors: Paul D. Ziegler, Minneapolis, MN (US); Shantanu Sarkar, Roseville, MN (US); Eduardo Warman, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 371 days.

(21) Appl. No.: 16/909,436

(22) Filed: Jun. 23, 2020

(65) Prior Publication Data

US 2020/0405155 A1   Dec. 31, 2020

Related U.S. Application Data

(60) Provisional application No. 62/868,141, filed on Jun. 28, 2019.

(51) Int. Cl.
*A61B 5/024* (2006.01)
*A61B 5/00* (2006.01)
*A61B 5/11* (2006.01)

(52) U.S. Cl.
CPC ............ *A61B 5/024* (2013.01); *A61B 5/4836* (2013.01); *A61B 5/686* (2013.01); *A61B 5/746* (2013.01); *A61B 5/1118* (2013.01)

(58) Field of Classification Search
CPC ....... A61B 5/024; A61B 5/4836; A61B 5/686; A61B 5/746; A61B 5/1118
See application file for complete search history.

(56) References Cited

U.S. PATENT DOCUMENTS

| | | | |
|---|---|---|---|
| 4,898,182 A * | 2/1990 | Hawkins | A61B 5/7264 600/509 |
| 6,190,324 B1 | 2/2001 | Kieval et al. | |
| 6,280,409 B1 | 8/2001 | Stone et al. | |
| 6,529,771 B1 | 3/2003 | Kieval et al. | |
| 6,904,313 B1 * | 6/2005 | Snell | A61B 5/0031 600/509 |
| 7,031,766 B1 | 4/2006 | Paris | |
| 7,043,294 B1 | 5/2006 | Paris | |
| 7,171,271 B2 | 1/2007 | Koh et al. | |
| 7,708,683 B2 * | 5/2010 | Hadley | A61B 5/352 600/15 |

(Continued)

OTHER PUBLICATIONS

International Search Report and Written Opinion from PCT/US2020/039345 dated Aug. 28, 2020, 8 pages.

(Continued)

*Primary Examiner* — Catherine M Voorhees
(74) *Attorney, Agent, or Firm* — Mueting Raasch Group

(57) ABSTRACT

Some aspects relate to systems, devices, and methods of assessing heart rate recovery. A heart rate of a patient may be measured during a plurality of heart rate recovery events. Each of the plurality of heart rate recovery events comprises a duration of time after an activity resulting in an elevated heart rate. Heart rate recovery information may be determined based on the measured heart rate during each of the plurality of heart rate recovery events and a cardiac status of the patient may be generated from the determined heart rate recovery information over the plurality of heart rate recovery events.

20 Claims, 9 Drawing Sheets

(56) References Cited

U.S. PATENT DOCUMENTS

| | | | | |
|---|---|---|---|---|
| 8,255,046 | B2* | 8/2012 | Sarkar | A61N 1/36521 600/509 |
| 8,708,924 | B2 | 4/2014 | Wariar et al. | |
| 10,448,849 | B2* | 10/2019 | Ferdosi | A61B 5/0245 |
| 2005/0038351 | A1* | 2/2005 | Starobin | A61B 5/352 600/516 |
| 2005/0065443 | A1* | 3/2005 | Ternes | A61B 5/02405 600/509 |
| 2009/0287103 | A1 | 11/2009 | Pillai | |
| 2010/0030293 | A1 | 2/2010 | Sarkar et al. | |
| 2019/0358464 | A1* | 11/2019 | Volosin | A61B 5/742 |

OTHER PUBLICATIONS

Cahalin et al., "Heart rate recovery after the 6 min walk test rather than distance ambulated is a powerful prognostic indicator in heart failure with reduced and preserved ejection fraction: a comparison with cardiopulmonary exercise testing," European Journal of Heart Failure, May 2013; 15(5):519-527.

Dimopoulos et al., "The Prognostic Role of Heart Rate Recovery after Exercise in Health and Disease," Austin J Cardiovasc Dis Atherosclerosis, 2015; 2(2):1-10.

Dimkpa, "Post-Exercise Heart Rate Recovery: An Index of Cardiovascular Fitness," Journal of Exercise Physiology, Feb. 2009; 12(1):10-22.

Karakulak et al., "Assessment of Cardiac Autonomic Nervous System Involvement in Systemic Sclerosis via Exercise Heart Rate Recovery," Med Prine Pract, 2015; 24:17-22.

Lanza et al., "Prognostic Value of Heart Rate Turbulence and its Relation to Inflammation in Patients With Unstable Angina Pectoris," The American Journal of Cardiology, Apr. 15, 2009; 103(8):1066-1072.

Tulppo et al., "Origin and Significance of Heart Rate Variability," Journal of the American College of Cardiology, Jun. 2004; 43(12):2278-80.

Yildiz et al., "Heart Rate Turbulence Analysis in Subclinical Hypothyroidism Heart Rate Turbulence in Hypothyroidism," Acta Cardiol Sin, 2015; 31:444-448.

* cited by examiner

HEART RATE RECOVERY ASSESSMENT

The present application claims the benefit of U.S. Provisional Application Ser. No. 62/868,141, filed Jun. 28, 2019, which is incorporated herein by reference in its entirety.

The present disclosure relates to systems, devices, and methods configured to assess patients generally, and particularly, patients with conditions such as, e.g., heart failure.

Heart failure (HF) is a complex disease that may be broadly defined by an inability of the heart to pump sufficiently to cope with its venous return and/or to deliver sufficient output to meet the metabolic demands of the body. Heart failure is an increasingly common, life-threatening cardiovascular disorder, characterized by marked disability, frequent hospitalization, and high mortality. HF is increasingly prevalent in older individuals (up to 10% of the population) and it has become the most common cause for hospitalization in people over 65 years of age. HF is a leading cause or contributor to hospitalization, and therefore, is emerging as a substantial contributor to healthcare spending.

Cardiac output is a function of stroke volume, a reflection of the pumping ability of the heart, and heart rate (HR). As people age, or in the presence of conditions that limit the heart's pumping ability, there is a progressive dependence on an increase in HR under conditions such as exercise, during which an increased cardiac output is required. Additionally, chronotropic incompetence (CI) (characterized by an inadequate rise in HR during exercise), the progression of chronic heart failure (CHF), the use of drugs in the treatment of CHF, hypertension, or other diseases may also develop and/or be reflective of a worsening cardiac status or drug side effect.

A patient's health can be assessed through medical history and physical examination to determine and track the progress of HF in a patient. This can involve much time and cost with the patient at the physician's office to establish a management program for the patient's treatment. Management programs can include pharmacological therapy such as beta-blockers, ACE inhibitors, and diuretics. More aggressive treatment can include biventricular pacing and other implantable cardiac device therapies. Management programs can also include an exercise routine.

Exercise diagnostics can be helpful in assessing the patient's health. During exercise, the heart rate is a parameter or indicator of the amount of work that was required to provide blood and oxygen to the body. The maximum heart rate for a level of exercise corresponds to the conditioning of the heart. Other parameters, such as heart rate intensity, percent oxygen consumption (% $VO_2$) reserve, metabolic equivalents (METS), and workload also provide data that is indicative of heart conditioning.

Measurements that track the patient's natural cardiac responsiveness to stress (e.g., exercise), such as heart rate recovery (HRR) can be useful in assessing the patient's health. Heart rate recovery after exercise can be evaluated as a clinical marker of good vagal activity and cardiac health. As the heart rate increases due to a reduction in vagal tone, the heart rate also decreases with a reactivation of vagal activity. A delayed response to the decreasing heart rate may be a good prognostic marker of overall mortality and cardiac health. Implantable or extracorporeal devices can be useful in providing physicians with diagnostic parameters to monitor the patient's medical condition.

Heart rate recovery includes a decrease in a heart rate of the patient indicating a ceasing of an elevated heart rate, for example, after the patient performs an exercise regime. Heart rate recovery events can be useful in demonstrating the health, or strength, of the heart. Patient data related to heart status and heart rate recovery can be obtained in a variety of ways. Typically, a patient directly conveys health data to medical personnel during an office visit, however, this can limit the time period over which the health data can be collected. Some data may be automatically generated and transmitted wirelessly to a computer system or health care system. A trend, or pattern, of measurements indicating changes within a patient, including heart rate recovery, can be useful to determine a patient's cardiac status and medical treatment.

SUMMARY

This disclosure generally relates to systems, devices, and methods to assess heart rate recovery to determine a cardiac status of a patient.

Some aspects, in accordance with principles of the present disclosure, relate to a method including measuring a heart rate of a patient during a plurality of heart rate recovery events. Each of the plurality of heart rate recovery events comprises a duration of time after an activity resulting in an elevated heart rate. The method also includes determining heart rate recovery information based on the measured heart rate during each of the plurality of heart rate recovery events and generating a cardiac status of the patient from the determined heart rate recovery information over the plurality of heart rate recovery events.

Other aspects, in accordance with principles of the present disclosure, relate to a device including a sensor apparatus and a processing apparatus. The sensor apparatus includes a heart rate sensor to sense a heart rate of a patient. The processing apparatus is operably coupled to the sensor apparatus. The processing apparatus includes processing circuitry configured to monitor a heart rate of a patient using the heart rate sensor during a plurality of heart rate recovery events, determine heart rate recovery information based on the measured heart rate during each of the plurality of heart rate recovery events, and generate a cardiac status of the patient from the determined heart rate recovery information over the plurality of heart rate recovery events. Each of the plurality of heart rate recovery events includes a duration of time after an activity resulting in an elevated heart rate.

Other aspects, in accordance with principles of the present disclosure, relate to a system including a sensing apparatus, a processing apparatus, and a notification apparatus. The sensor apparatus includes a heart rate sensor to sense a heart rate of a patient. The processing apparatus is operably coupled to the sensor apparatus. The processing apparatus includes processing circuitry configured to monitor a heart rate of a patient using the heart rate sensor during a plurality of heart rate recovery events, determine heart rate recovery information based on the measured heart rate during each of the plurality of heart rate recovery events, and generate a cardiac status of the patient from the determined heart rate recovery information over the plurality of heart rate recovery events. Each of the plurality of heart rate recovery events includes a duration of time after an activity resulting in an elevated heart rate. The notification apparatus is to notify the patient initiate an activity resulting in the elevated heart rate.

Other aspects, in accordance with principles of the present disclosure, relate to a method including measuring a perturbation effect of a patient during a plurality of perturbation recovery events, determining perturbation recovery information based on the measured perturbation effect during each of the plurality of perturbation recovery events, and generating a cardiac status of the patient from the determined perturbation recovery information over the plurality of perturbation recovery events. Each of the plurality of perturbation recovery events comprises a duration of time after the patient is perturbed.

Other aspects, in accordance with principles of the present disclosure, relate to a device including a sensor apparatus and a processing apparatus. The sensor apparatus includes a heart rate sensor to sense a heart rate of a patient. The processing apparatus is operably coupled to the sensor apparatus. The processing apparatus includes processing circuitry configured to measure a perturbation effect of a patient during a plurality of perturbation recovery events, determine perturbation recovery information based on the measured perturbation effect during each of the plurality of perturbation recovery events, and generate a cardiac status of the patient from the determined perturbation recovery information over the plurality of perturbation recovery events. Each of the plurality of perturbation recovery events comprises a duration of time after the patient is perturbed.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or apparatus for purposes of clarity, it should be understood that the techniques of this disclosure may be performed by a combination of units or apparatuses associated with, for example, an implantable medical device.

Illustrative cardiac therapy systems and devices may be further described herein with reference to FIGS. 1-3B that may utilize the illustrative systems, methods, and processes described herein with respect to FIGS. 4-7.

Figure 1:
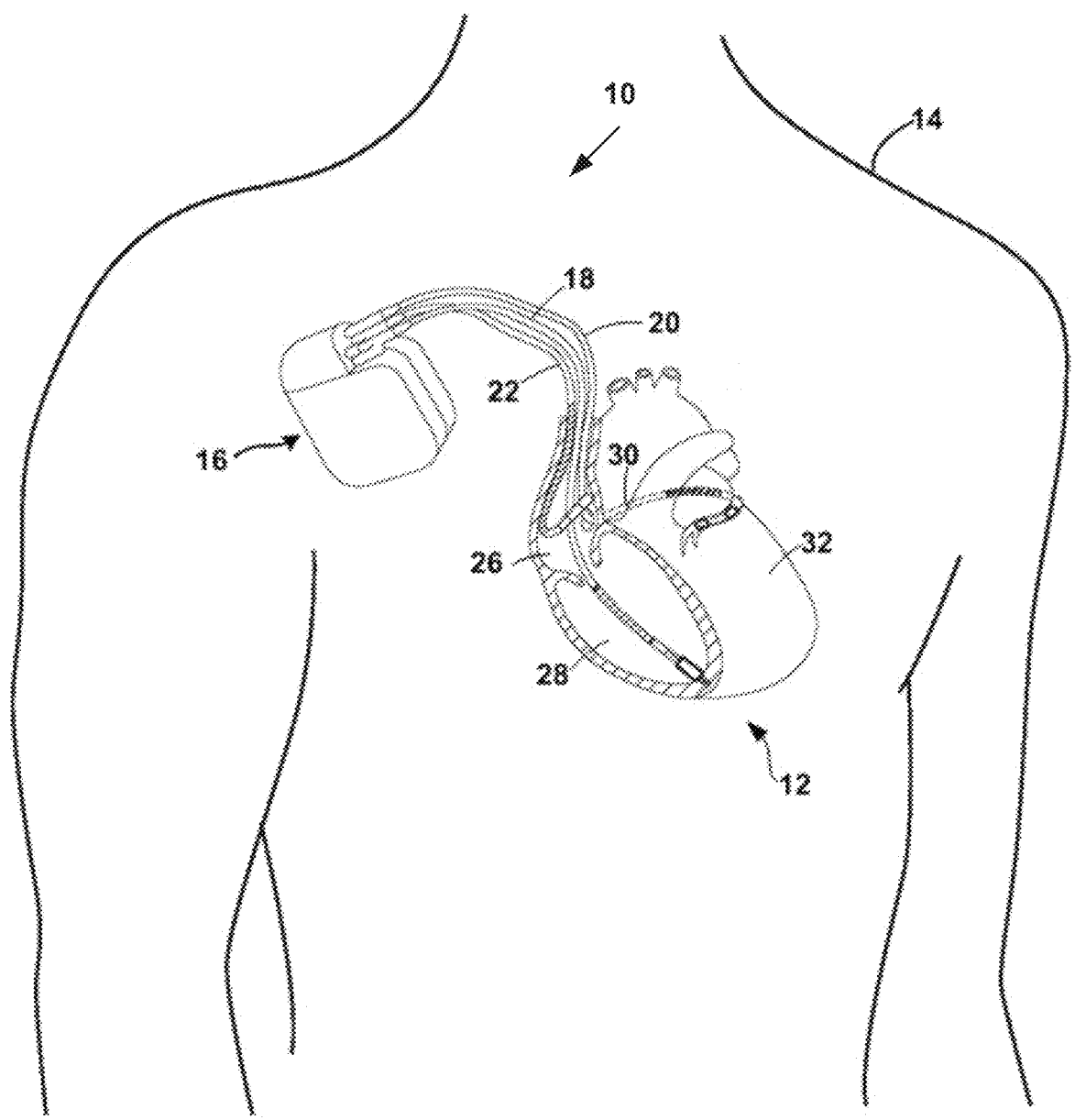
FIG. 1 is a diagram of an illustrative system including an illustrative implantable medical device (IMD).

FIG. 1 is a conceptual diagram illustrating an illustrative therapy system 10 that may be used to deliver pacing therapy to a patient 14. Patient 14 may, but not necessarily, be a human. The therapy system 10 may include an implantable medical device 16 (IMD), which may be coupled to leads 18, 20, 22. The IMD 16 may be, e.g., an implantable pacemaker, cardioverter, and/or defibrillator, that delivers, or provides, electrical signals (e.g., paces, etc.) to and/or senses electrical signals from the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., A-V delay and other various timings, pulse wide, amplitude, voltage, burst length, etc. Further, the IMD 16 may be operable to use various electrode configurations to deliver pacing therapy, which may be unipolar, bipolar, quadripolar, or further multipolar. For example, a multipolar lead may include several electrodes that can be used for delivering pacing therapy. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the IMD. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

Figure 2A:
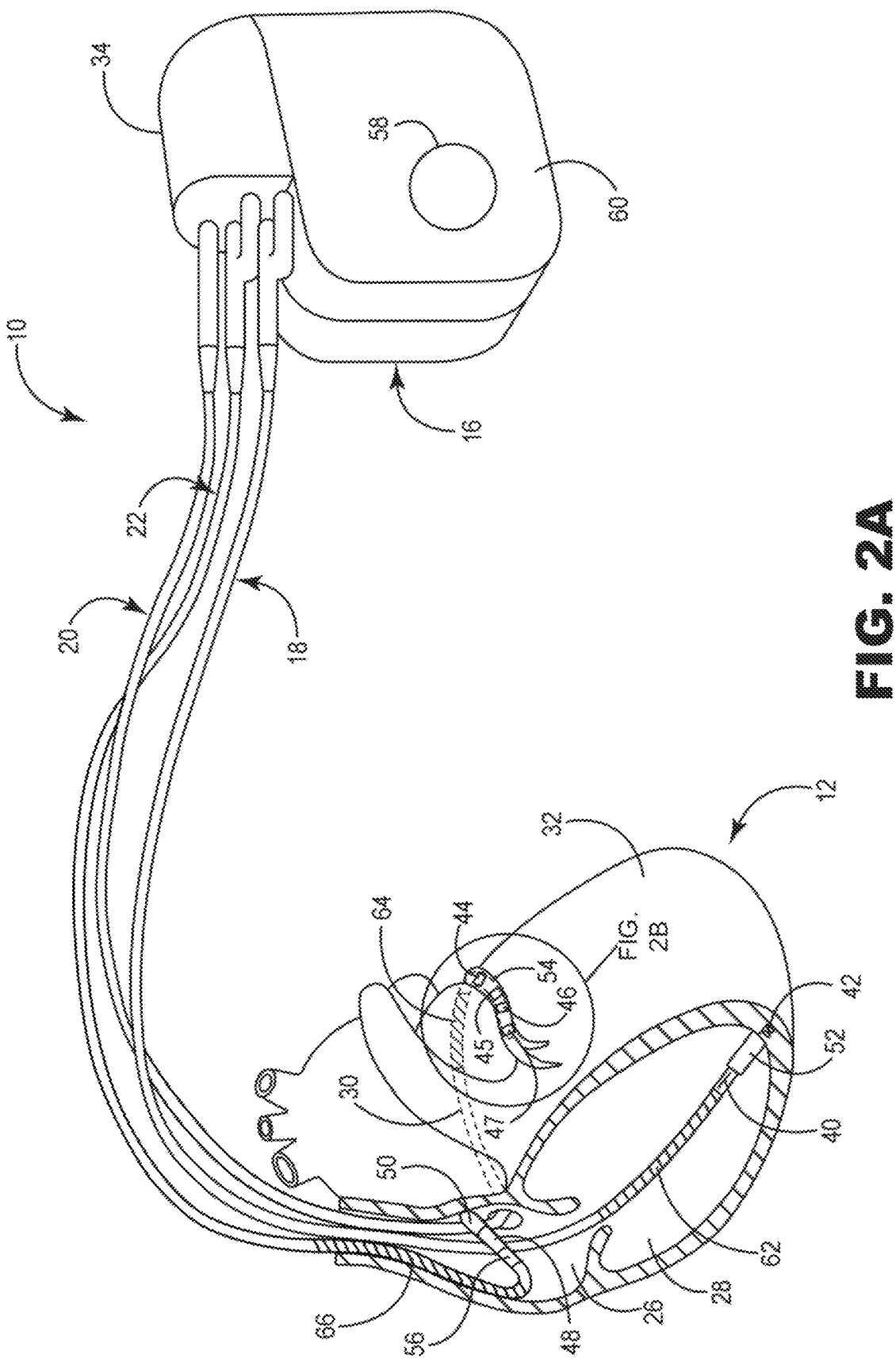
FIG. 2A is a diagram of the illustrative IMD of FIG. 1.
Figure 2B:
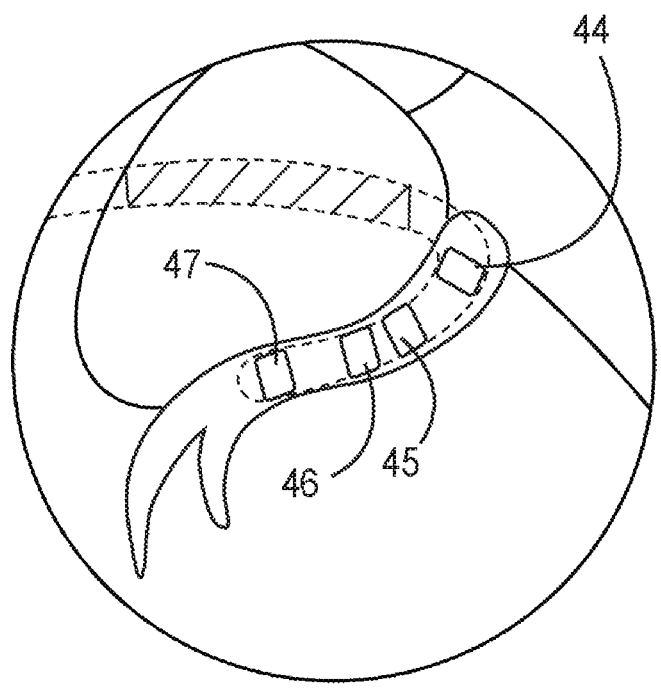
FIG. 2B is a diagram of an enlarged view of a distal end of the electrical lead disposed in the left ventricle of FIG. 2A

FIGS. 2A-2B are conceptual diagrams illustrating the IMD 16 and the leads 18, 20, 22 of therapy system 10 of FIG. 1 in more detail. The leads 18, 20, 22 may be electrically coupled to a therapy delivery module (e.g., for delivery of pacing therapy), a sensing module (e.g., for sensing one or more signals from one or more electrodes), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, bipolar electrodes 44, 45, 46, 47 are located proximate to a distal end of the lead 20 and bipolar electrodes 48, 50 are located proximate to a distal end of the lead 22.

The electrodes 40, 44, 45, 46, 47, 48 may take the form of ring electrodes, and the electrodes 42, 50 may take the form of extendable helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to a respective one of the electrical contacts on the proximal end of the leads 18, 20, 22.

Additionally, electrodes 44, 45, 46 and 47 may have an electrode surface area of about 5.3 mm$^2$ to about 5.8 mm$^2$. Electrodes 44, 45, 46, and 47 may also be referred to as LV1, LV2, LV3, and LV4, respectively. The LV electrodes (i.e., left ventricle electrode 1 (LV1) 44, left ventricle electrode 2 (LV2) 45, left ventricle electrode 3 (LV3) 46, and left ventricle 4 (LV4) 47 etc.) on the lead 20 can be spaced apart at variable distances. For example, electrode 44 may be a distance of, e.g., about 21 millimeters (mm), away from electrode 45, electrodes 45 and 46 may be spaced a distance of, e.g. about 1.3 mm to about 1.5 mm, away from each other, and electrodes 46 and 47 may be spaced a distance of, e.g. 20 mm to about 21 mm, away from each other.

The electrodes 40, 42, 44, 45, 46, 47, 48, 50 may further be used to sense electrical signals (e.g., morphological waveforms within electrograms (EGM)) attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. In some examples, as illustrated in FIG. 2A, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 45, 46, 47, 48, 50 may be used for unipolar sensing or pacing in combination with the housing electrode 58. It is generally understood by those skilled in the art that other electrodes can also be selected to define, or be used for, pacing and sensing vectors. Further, any of electrodes 40, 42, 44, 45, 46, 47, 48, 50, 58, when not being used to deliver pacing therapy, may be used to sense electrical activity during pacing therapy.

As described in further detail with reference to FIG. 2A, the housing 60 may enclose a therapy delivery module that may include a stimulation generator for generating cardiac pacing pulses and defibrillation or cardioversion shocks, as well as a sensing module for monitoring the electrical signals of the patient's heart (e.g., the patient's heart rhythm). The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity and may be used in combination with any of electrodes 40, 42, 44, 45, 46, 47, 48, 50, 58. In at least one embodiment, the RV elongated electrode 62 may be used to sense electrical activity of a patient's heart during the delivery of pacing therapy (e.g., in combination with the housing electrode 58, or defibrillation electrode-to-housing electrode vector).

The configuration of the illustrative therapy system 10 illustrated in FIGS. 1-3B is merely one example. In other examples, the therapy system may include epicardial leads and/or patch electrodes instead of or in addition to the transvenous leads 18, 20, 22 illustrated in FIG. 1. Additionally, in other examples, the therapy system 10 may be implanted in and/or around the cardiac space without transvenous leads (e.g., leadless/wireless pacing systems) or with leads implanted (e.g., implanted transvenously or using approaches) into the left chambers of the heart (in addition to or replacing the transvenous leads placed into the right chambers of the heart as illustrated in FIG. 1). Further, in one or more embodiments, the IMD 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 1-3B. Still further, other therapy systems may include a single lead that extends from the IMD 16 into the right atrium 26 or the right ventricle 28, or two leads that extend into a respective one of the right atrium 26 and the right ventricle 28.

Figure 3A:
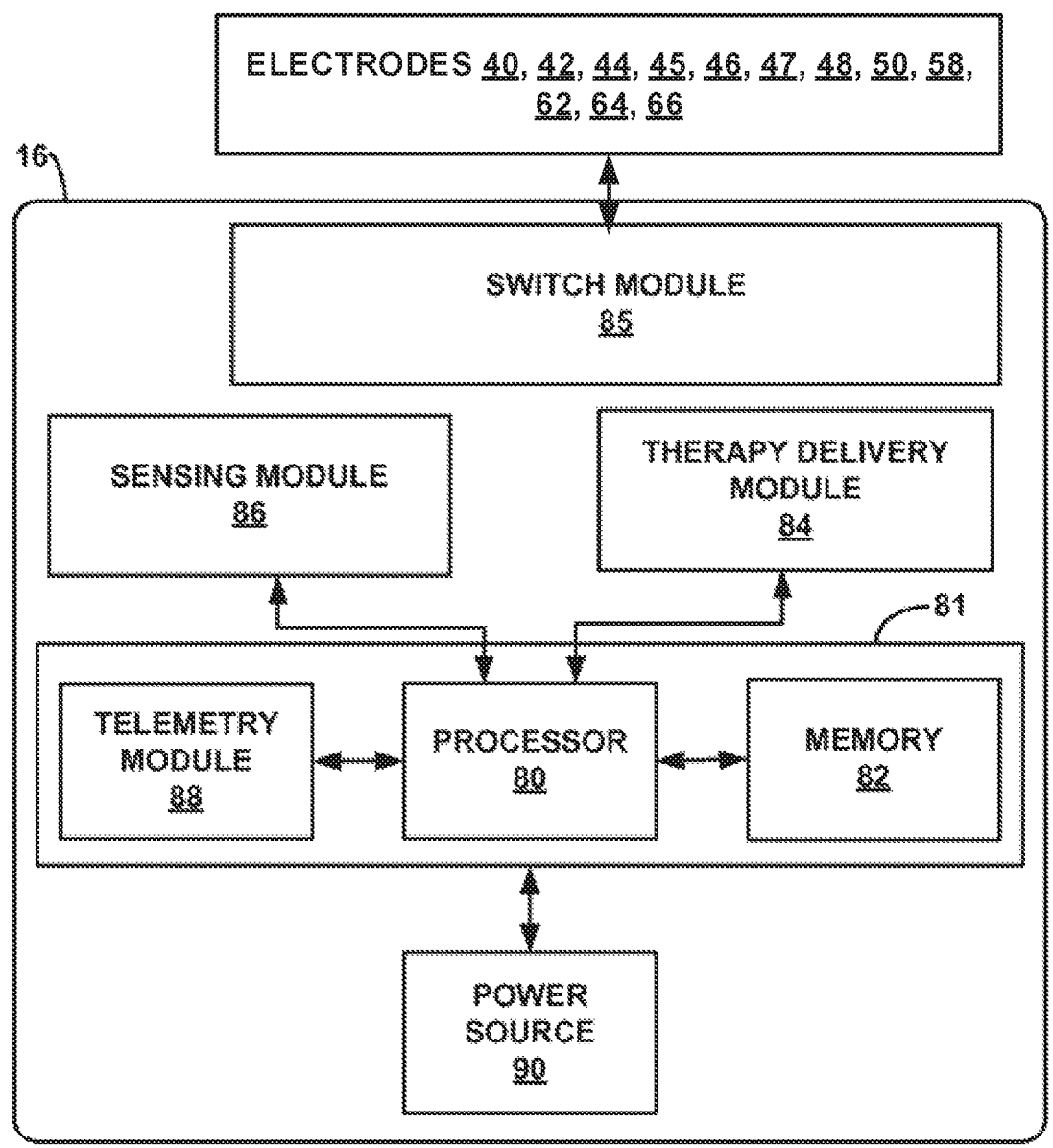
FIG. 3A is a block diagram of an illustrative IMD, e.g., of the systems of FIGS. 1-2B.

FIG. 3A is a functional block diagram of one illustrative configuration of the IMD 16. As shown, the IMD 16 may include a control module 81, a therapy delivery module 84 (e.g., which may include a stimulation generator), a sensing module 86, and a power source 90. The control module, or apparatus, 81 may include a processor 80, memory 82, and a telemetry module, or apparatus, 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random-access memory (RAM), read-only memory (ROM), non-volatile RAM (NVRAM), electrically-erasable programmable ROM (EEPROM), flash memory, and/or any other digital media.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module, or apparatus, 84 to deliver therapy (e.g., electrical stimulation therapy such as pacing) to the heart 12 according to a selected one or more therapy programs, which may be stored in the memory 82. More, specifically, the control module 81 (e.g., the processor 80) may control various parameters of the electrical stimulus delivered by the therapy delivery module 84 such as, e.g., A-V delays, V-V delays, pacing pulses with the amplitudes, pulse widths, frequency, or electrode polarities, etc., which may be specified by one or more selected therapy programs (e.g., A-V and/or V-V delay adjustment programs, pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, the therapy delivery module 84 may deliver pacing stimulus (e.g., pacing pulses) via ring electrodes 40, 44, 45, 46, 47, 48 coupled to leads 18, 20, 22 and/or helical tip electrodes 42, 50 of leads 18, 22. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured to deliver one or more of these types of stimulation in the form of other signals, such as sine waves, square waves, and/or other substantially continuous time signals.

The IMD 16 may further include a switch module, or apparatus, 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module, or apparatus, 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a bipolar or multipolar pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may also be used with the sensing module 86 to select which of the available electrodes are used, or enabled, to, e.g., sense electrical activity of the patient's heart (e.g., one or more electrical vectors of the patient's heart using any combination of the electrodes 40, 42, 44, 45, 46, 47, 48, 50, 58, 62, 64, 66). Likewise, the switch module 85 may also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 42, 44, 45, 46, 47, 48, 50, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit.

In some examples, the control module 81 may operate as an interrupt-driven device and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding one or more series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as a programmer. For example, under the control of the processor 80, the telemetry module 88 may receive downlink telemetry from and send uplink telemetry to a programmer with the aid of an antenna, which may be internal and/or external. The processor 80 may provide the data to be uplinked to a programmer and the control signals for the telemetry circuit within the telemetry module 88, e.g., via an address/data bus. In some examples, the telemetry module 88 may provide received data to the processor 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 3B:
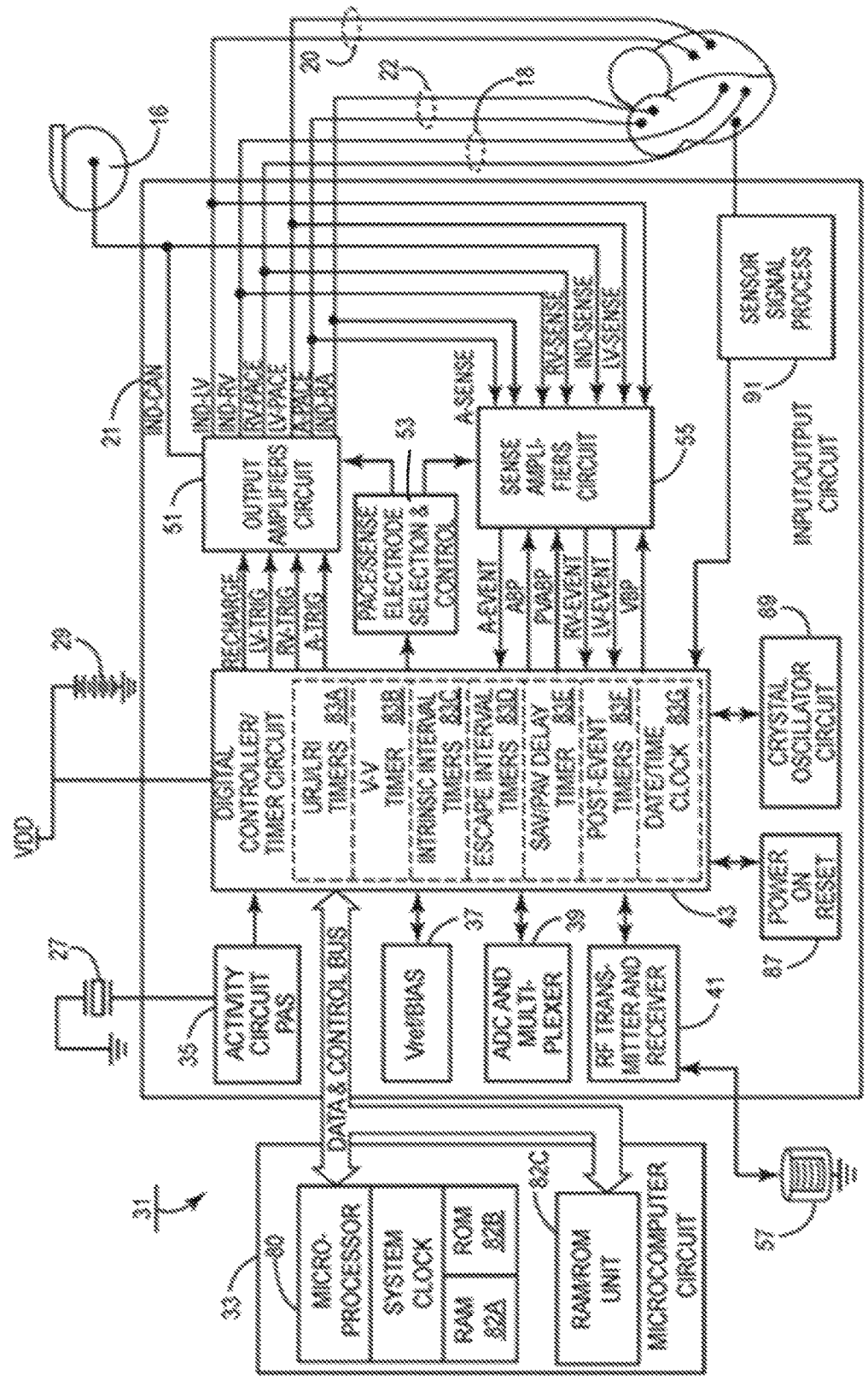
FIG. 3B is another block diagram of an illustrative IMD (e.g., an implantable pulse generator) circuitry and associated leads employed in the systems of FIGS. 1-2B.

FIG. 3B is another embodiment of a functional block diagram for IMD 16 that depicts bipolar RA lead 22, bipolar RV lead 18, and bipolar LV CS lead 20 without the LA CS pace/sense electrodes and coupled with an implantable pulse generator (IPG) circuit 31 having programmable modes and parameters of a bi-ventricular DDD/R type known in the pacing art. In turn, the sensor signal processing circuit 91 indirectly couples to the timing circuit 43 and via data and control bus to microcomputer circuitry 33. The IPG circuit 31 is illustrated in a functional block diagram divided generally into a microcomputer circuit 33 and a pacing circuit 21. The pacing circuit 21 includes the digital controller/timer circuit 43, the output amplifiers circuit 51, the sense amplifiers circuit 55, the RF telemetry transceiver 41, the activity sensor circuit 35 as well as a number of other circuits and components described below.

Crystal oscillator circuit 89 provides the basic timing clock for the pacing circuit 21 while battery 29 provides power. Power-on-reset circuit 87 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21. Analog-to-digital converter (ADC) and multiplexer circuit 39 digitize analog signals and voltage to provide, e.g., real time telemetry of cardiac signals from sense amplifiers 55 for uplink transmission via RF transmitter and receiver circuit 41. Voltage reference and bias circuit 37, ADC and multiplexer 39, power-on-reset circuit 87, and crystal oscillator circuit 89 may correspond to any of those used in illustrative implantable cardiac pacemakers.

If the IPG is programmed to a rate responsive mode, the signals output by one or more physiologic sensors are employed as a rate control parameter (RCP) to derive a physiologic escape interval. For example, the escape interval is adjusted proportionally to the patient's activity level developed in the patient activity sensor (PAS) circuit 35 in the depicted, illustrative IPG circuit 31. The patient activity sensor 27 is coupled to the IPG housing and may take the form of a piezoelectric crystal transducer. The output signal of the patient activity sensor 27 may be processed and used as an RCP. Sensor 27 generates electrical signals in response to sensed physical activity that are processed by activity circuit 35 and provided to digital controller/timer circuit 43. Similarly, the illustrative systems, apparatus, and methods described herein may be practiced in conjunction with alternate types of sensors such as oxygenation sensors, pressure sensors, pH sensors, and respiration sensors, perfusion sensors, heart rate sensors, for use in providing rate responsive pacing capabilities. Alternately, QT time may be used as a rate indicating parameter, in which case no extra sensor is required. Similarly, the illustrative embodiments described herein may also be practiced in non-rate responsive pacemakers.

Data transmission to and from the external programmer is accomplished by way of the telemetry antenna 57 and an associated RF transceiver 41, which serves both to demodulate received downlink telemetry and to transmit uplink telemetry. Uplink telemetry capabilities may include the ability to transmit stored digital information, e.g., operating modes and parameters, EGM histograms, and other events, as well as real time EGMs of atrial and/or ventricular electrical activity and marker channel pulses indicating the occurrence of sensed and paced depolarizations in the atrium and ventricle.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 43 and A-EVENT, RV-EVENT, and LV-EVENT signals generated by sense amplifiers circuit 55, among others. The specific values of the intervals and delays timed out by digital controller/timer circuit 43 are controlled by the microcomputer circuit 33 by way of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative A-V delay intervals, V-V delay intervals, and the energy delivered to each ventricle and/or atrium.

In one embodiment, microprocessor 80 is a custom microprocessor adapted to fetch and execute instructions stored in RAM/ROM unit 82 in a conventional manner. It is contemplated, however, that other implementations may be suitable to practice the present disclosure. For example, an off-the-shelf, commercially available microprocessor or microcontroller, or custom application-specific, hardwired logic, or state-machine type circuit may perform the functions of microprocessor 80.

Digital controller/timer circuit 43 operates under the general control of the microcomputer 33 to control timing and other functions within the pacing circuit 21 and includes a set of timing and associated logic circuits of which certain ones pertinent to the present disclosure are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an A-V delay interval timer 83E for timing the A-LVp delay (or A-RVp delay) from a preceding A-EVENT or A-TRIG, a post-ventricular timer 83F for timing post-ventricular time periods, and a date/time clock 83G.

The A-V delay interval timer 83E is loaded with an appropriate delay interval for one ventricular chamber (e.g., either an A-RVp delay or an A-LVp) to time-out starting from a preceding A-PACE or A-EVENT. The interval timer 83E triggers pacing stimulus delivery and can be based on one or more prior cardiac cycles (or from a data set empirically derived for a given patient).

The post-event timer 83F times out the post-ventricular time period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include a post-ventricular atrial blanking period (PVARP), a post-atrial ventricular blanking period (PAVBP), a ventricular blanking period (VBP), and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any A-V delay, and an atrial blanking period (ABP) during which atrial sensing is disabled. It should be noted that the starting of the post-atrial time periods and the A-V delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates A-V delays, V-V delays, post-ventricular time periods, and post-atrial time periods that vary with the sensor-based escape interval established in response to the RCP(s) and/or with the intrinsic atrial and/or ventricular rate.

The output amplifiers circuit 51 contains a RA pace pulse generator (and a LA pace pulse generator if LA pacing is provided), a RV pace pulse generator, a LV pace pulse generator, and/or any other pulse generator configured to provide atrial and ventricular pacing. In order to trigger generation of an RV-PACE or LV-PACE pulse, digital controller/timer circuit 43 generates the RV-TRIG signal at the time-out of the A-RVp delay (in the case of RV pre-excitation) or the LV-TRIG at the time-out of the A-LVp delay (in the case of LV pre-excitation) provided by A-V delay interval timer 83E (or the V-V delay timer 83B). Similarly, digital controller/timer circuit 43 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the IND-CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 43 controls sensitivity settings of the atrial and ventricular sense amplifiers 55.

The sense amplifiers may be uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV, and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 43. Similarly, left atrial depolarizations or P-waves in the LA-SENSE signal that are sensed by the LA sense amplifier, if provided, result in a LA-EVENT signal that is communicated to the digital controller/timer circuit 43. Ventricular depolarizations or R-waves in the RV-SENSE signal are sensed by a ventricular sense amplifier result in an RV-EVENT signal that is communicated to the digital controller/timer circuit 43. Similarly, ventricular depolarizations or R-waves in the LV-SENSE signal are sensed by a ventricular sense amplifier result in an LV-EVENT signal that is communicated to the digital controller/timer circuit 43. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

The techniques described in this disclosure, including those attributed to the IMD 16 and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The illustrative devices, systems, and methods may be used to generate a cardiac status, or cardiac trend, based on a patient's cardiac health in accordance with the present disclosure. The cardiac status can provide useful information of a trend, or pattern, in the patient's cardiac health determined over an extended period of time. The cardiac status of a patient can be useful in assessing and quantifying the health of the patient, in particular, the health of the patient's heart, as well as being useful in evaluating and managing a patient's treatment and cardiac management care. For example, the illustrative devices, systems, and methods may be used to assist in the configuration and/or adjustment of one or more cardiac therapy settings of a cardiac therapy delivered to a patient such as, e.g., optimization of the A-V interval, or delay, of pacing therapy (e.g., left ventricular-only, or left univentricular, pacing therapy) and the A-V interval, or delay, and the V-V interval, or delay, of pacing therapy (e.g., biventricular pacing therapy). In another example, the illustrative devices, systems, and methods may be used to assist in the configuration and/or adjustment of a pharmaceutical therapy being delivered to the patient in response to the patient's cardiac status. In another example, the illustrative device, systems, and methods may be used to assist in the configuration and/or adjustment of a physical therapy of a patient in response to the patient's cardiac status.

A cardiac status, as described further below, can be useful in correlating decreased physical activity with an undesirable patient condition such as the onset or progression of heart failure, for example. The devices, systems, and methods may be generally described as being used to quantify and assess a patient's bodily response(s) to a perturbation, for example, and to generate a cardiac status of a patient based on data generated from a plurality of the patient's bodily responses to the perturbation, for example. An underlying presumption of heart rate recovery is that the heart rate of a patient will increase correspondingly with an increase in activity. However, there may be occurrences wherein the heart rate does not increase correspondingly to increased activity and an undesirable patient condition can be determined.

In this regard, one example of a perturbation can be a deviation in a regular heart rate of a patient. Perturbations, however, can occur in different manners, or forms, and at different time scales (beats to minutes, to hours, to days). Some examples of perturbations include a syncopal event (e.g., a cardiac pause) or a premature depolarization (atrial or ventricular), or a bout of pneumonia. Other health statuses (e.g., disease states) to consider can include chronic obstructive pulmonary disease (COPD) status and anemia status. Other examples of perturbations, particularly for HF patients, can include strenuous activity (e.g., exercise) or an arrhythmia.

Figure 4:
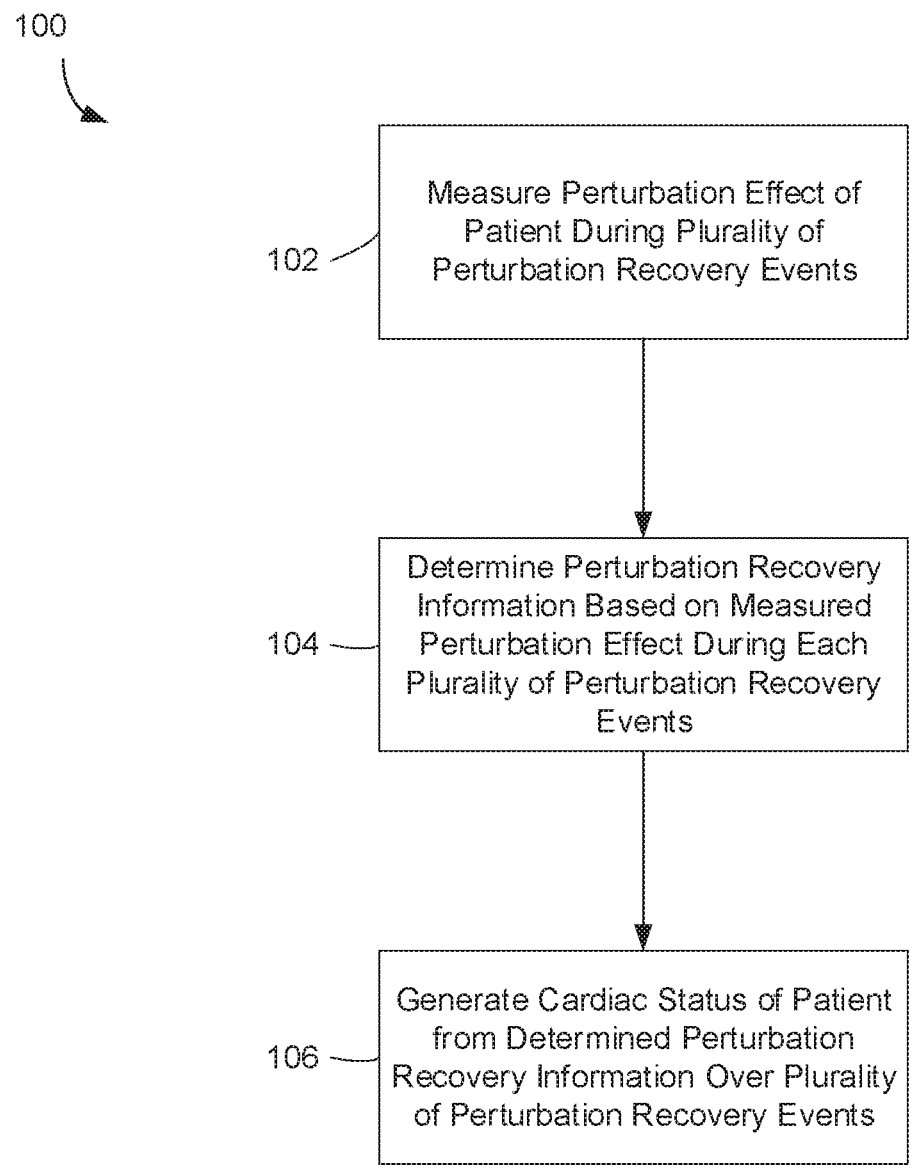
FIG. 4 illustrates a flow diagram of an example method of generating a cardiac status of a patient in accordance with aspects of the present disclosure.

FIG. 4 illustrates a flow diagram of an example method 100 of generating a cardiac status of a patient using perturbation recovery information. A perturbation of the heart can cause the oxygen demand within the patient's body to increase. In response to the perturbation, increased cardiac output can be required to supply more oxygen to the organs and/or tissues having increased oxygen demand. More oxygen can be supplied by either inputting more oxygen to lungs (e.g., by breathing faster and/or harder) or improving the efficiency of transporting the oxygen to the organs in need. One manner of improving efficiency of transporting the oxygen to the organs is by increasing cardiac output. Cardiac output is a function of volume (SV), a reflection of the pumping ability of the heart, and heart rate (HR). Cardiac output can be increased via increasing the stroke volume (e.g., volume of blood pumped from the left ventricle per beat) and/or the heart rate (e.g., beats per minute of the heart) of the patient. The method 100 may include, at 102, measuring a perturbation effect during each of a plurality of perturbation recovery events. Measurements that track the patient's natural, or normal, cardiac responsiveness to stress (e.g., perturbation), such as heart rate recovery (HRR), can be measured, for example. During a heart rate recovery, a heart rate of the patient typically decreases over a duration of time after an activity resulting in an elevated heart rate (e.g., a heart rate peak activity, or perturbation).

In a normal healthy person, the bodily responses to a perturbation have a typical, or normal, response time, degree of change, and pattern of change (e.g., time course of change signal morphology). In acute or chronic disease states, these bodily responses will vary from the typical bodily responses experienced by a normal healthy person. For example, in a patient with Acute HF, exacerbation following a sudden increase in exercise resulting in a significantly larger increase in heart rate, may take longer to recover and return to a baseline. The HF patient heart typically does not function as well as a patient without HF, so the heart of the HF patient may have to maintain an elevated heart rate for a longer duration of time to compensate, which may often result in decompensated heart failure. Similarly, the patient's respiration may include faster and/or harder breathing for an extended period of time following a sudden increase in exercise.

After a perturbation to a cardiovascular system, the patient's body reacts through compensatory mechanisms to cope with the perturbation and return the cardiovascular system to its pre-perturbation state and/or prepare for another perturbation. In other words, the patient's body reacts to recover from the perturbation during a perturbation recovery event, or period of time after the patient is perturbed. As a patient develops a chronic illness, the patient's body may be unable to return the cardiovascular system to normal or may take more than a typical time period (or different temporal profile, but same or less amount of time) to return to equilibrium during the perturbation recovery event. The method 100 may include, at 104, determining perturbation recovery information, or data, based on the measured perturbation effect during each of the plurality of perturbation recovery events. The perturbation recovery information can include any information related to a patient's heart health. For example, perturbation recovery information can include a difference in the patient's respiration or heart rate over a period of time, a duration of time for the patient's respiration or heart rate to return to a baseline, or a duration of time for the patient's respiration or heart rate to return to another predetermined level, etc. The method 100 may further include, at 106, generating a cardiac status of the patient based on the perturbation recovery information from the plurality of perturbation recovery events, as described further below.

Figure 5A:
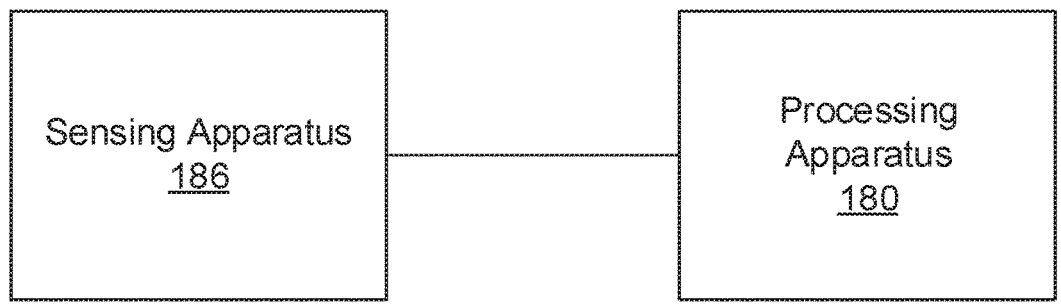
FIG. 5A is an illustrative block diagram of a device useful in determining heart rate recovery information and generating a cardiac status of a patient in accordance with aspects of the present disclosure.

FIG. 5A is an illustrative block diagram of a device 150 useful in determining heart rate recovery information and generating a cardiac status of a patient in accordance with aspects of the present disclosure. The device 150 can be an external device or an internal, implantable, device. There are various types of devices 150, both implantable and external, that can be used to monitor patient information in accordance with aspects of the present disclosure. Some non-limiting examples of suitable implantable devices include pacemakers, Implantable Cardioverter/Defibrillators (ICDs), cardiac resynchronization therapy (CRT) devices, insertable cardiac monitors, subcutaneous devices, and non-therapeutic monitoring devices. Examples of suitable external devices include smart wristbands, patches, smart watches, chest bands, devices used in conjunction with smart phones, or smart phones themselves.

The device 150 can be useful in sensing and monitoring various patient health status information such as, e.g., a patient's heart rate, activity level, heart rate variability, arrhythmia status, respiration rate, fluid status, etc. Patient health status information can be stored and/or transmitted to another device to generate patient alarms and to provide feedback to a clinician regarding the patient. Such information can be useful to optimize the patient's therapy device and to manage the patient's health. In one example, the device 150 can generate, or can be used to generate, a cardiac status using heart rate recovery information determined over a plurality of heart rate recovery events, as described further below.

The device 150 can include a sensing apparatus 186 and a processing apparatus 180. The sensing apparatus 186 can include a variety of sensors to sense one or more pieces of data from the patient that may be useful for generating a cardiac status of a patient such as, e.g., a heart rate and activity level of a patient. The sensing apparatus 186 may be similar to the sensors described above with respect to sensing module 86, and also as further described below. The processing apparatus 180 can include processing circuitry, similar to the processing circuitry described above with respect to processor 80, and also as further described below.

In one example, the device 150 can use sensing apparatus 186 to sense, process, and monitor activity information such as patient movement information based on accelerometer signals, pulse wave velocity signals, electrocardiogram signals, intracardiac electrogram signals, blood pressure measurement, and/or perfusion rate, for example. In other words, the sensing apparatus 186 can include activity sensors to collect activity values, levels, and signals. In one example, the sensing apparatus 186 includes an accelerometer as well as other suitable sensors.

Further, the sensing apparatus 186 can include sensors for measuring pressure, temperature, posture, impedance, and the like, as well as various combinations of such sensor signal output. Still further, the sensing apparatus 186 can include sensors to sense heart rate, activity level, and other biological information of a patient. In some examples, the sensing apparatus 186 can sense and measure at least one of a patient's respiration rate and effort, heart rate and short-term heart rate variability, blood pressure, and short-term fluid shifts. The sensed measurement(s) can be transmitted from the sensing apparatus 186 to the processing apparatus 180 for processing in order to quantify the patient's bodily response(s) to a perturbation such as, for example, to generate a cardiac status of a patient.

The processing apparatus 180 can determine heart rate recovery information for each of the plurality of heart rate recovery events and determine a trend of the determined heart rate recovery information over the plurality of heart rate recovery events to generate a cardiac status of the patient. Each heart rate recovery can be termed a "heart rate recovery event." In one example, the processing apparatus 180 can be employed to determine a heart rate recovery of a patient over each of a plurality of heart rate recovery events based on a sensed heart rate and activity level received from the sensing apparatus 186, for example. Each of the plurality of heart rate recovery events includes a decrease in a heart rate of the patient over a duration of time after an activity resulting an elevated heart rate for a prescribed period of time (e.g., a heart rate peak activity). For example, the patient's heart rate increases during an exercise regime; upon ceasing the exercise regime, the patient's heart rate decreases from the increased heart rate to a lower heart rate (e.g., pre-increased heart rate) over a determined period of time. In some embodiments, the processing apparatus 180 can determine initiation and termination of the activity resulting in an elevated heart rate based on, e.g., heart rate peak activity.

A cardiac status can be generated based upon, at least some of, the plurality of heart rate recovery events. The generated cardiac status can provide trend and diagnostic information regarding the patient's heart. The processing apparatus 180 can determine a heart risk score of the patient based on the generated cardiac status. The processing apparatus 180 can determine a pacing rate of a cardiac therapy to be delivered by a pacing device to a heart of a patient based on the generated pattern/trend. The pacing device can be an additional device to device 150 or can be the same device. In some examples, the patient having an implanted cardiac therapy device (i.e., pacing device) will have pacing suspended during the heart rate recovery events and activation of the sensing apparatus 186 monitoring the heart rate recovery events. In some examples, the system 200 can include a plurality of electrodes and therapy delivery circuitry operably coupled to the plurality of electrodes (not shown) to deliver cardiac therapy to a heart of the patient based the generated cardiac status.

Figure 5B:
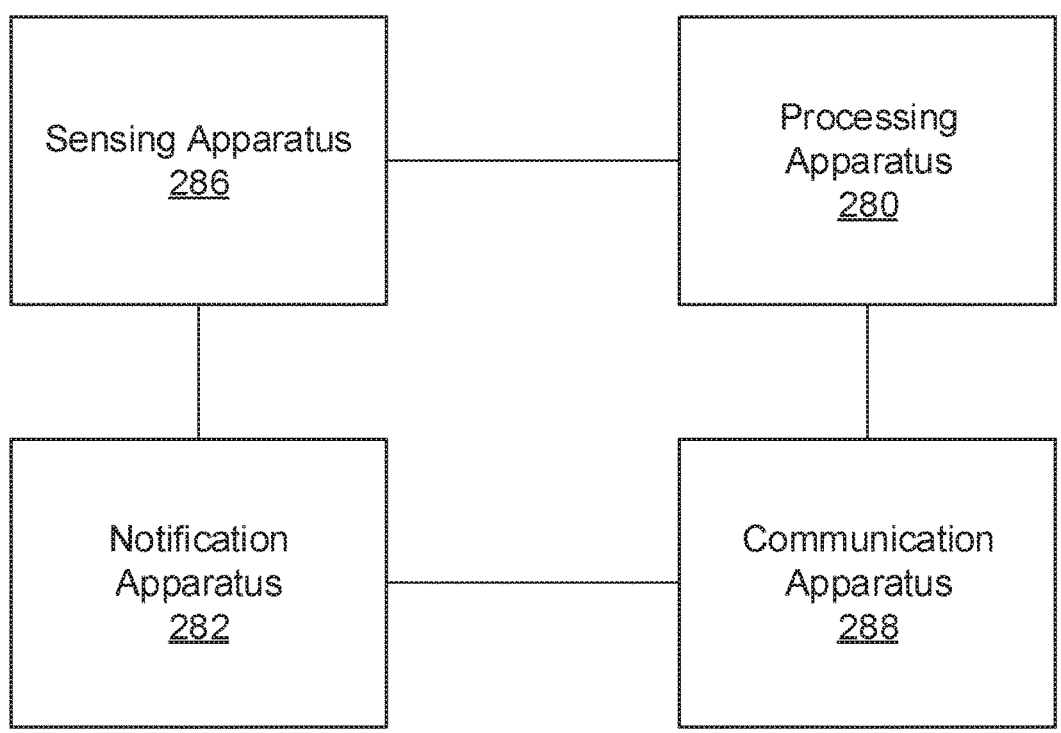
FIG. 5B is an illustrative block diagram of a system useful in determining heart rate recovery information and generating a cardiac status of a patient in accordance with aspects of the present disclosure.

FIG. 5B is an illustrative block diagram of a system 200 useful in determining heart rate recovery information and generating a cardiac status of a patient in accordance with aspects of the present disclosure. The system 200 includes a sensing apparatus 286 and a processing apparatus 280, similar to the sensing apparatus 186 and the processing apparatus 180 described above. In this example, the system 200 also includes a notification apparatus 282 and a communication apparatus 288. One or more of the sensing apparatus 286, the processing apparatus 280, the notification apparatus 282, and the communication apparatus 288 can be included in one or more implantable or external devices. For example, the apparatuses 286, 280, 282, and 288 can be included in single device 150, such as an external patch or ICD. In another example, the notification apparatus 282 and the communication apparatus 288 can be included in a one device (e.g., smart wristband) and the sensing apparatus 286 and the processing apparatus 280 can be included in another device (e.g., a subcutaneous device). Other types and combinations of inclusion of the apparatuses 286, 280, 282, and 288 in device(s) are also acceptable.

In some examples, the communication apparatus 288 can be used to transmit, or communicate, activity information, heart rate recovery information, and/or cardiac status of the patient from the system 200 to a physician located remote of the patient (e.g., physician's office when patient is not at physician's office) or the internet (e.g., cloud), etc. The communication can be over a network, such as a local-area network (LAN) and/or a wide-area network (WAN). The communication network can include an intranet communication network, an Internet communication network or a similar high-speed communication network including a wireless communication network.

In some examples, the transmitted communication can also include alerts, status updates, medical device adjustment notifications, and other informative communications. In some examples, the communication apparatus 288 illustrated in FIG. 5B can be configured to communicate the heart rate recovery information, cardiac status, prompts, alerts, or any other information externally to another device (e.g., computing device such as a server, a smart watch, a smart phone, tablet). The devices can store data, programs, instruction, or any other machine-readable data.

In some examples, the notification apparatus 282 can be used to signal, or notify, the patient to initiate and/or terminate an activity (e.g., exercise regime). For example, the notification apparatus 282 can be employed to prompt the patient to begin or terminate a specified exercise regime for a period of time. The notification apparatus 282 can provide tactile, auditory, visual or a combination of tactile, auditory, and visual notifications to the user.

In one example, prior to initiating notification via the notification apparatus 282 for a patient to begin an activity, the sensing apparatus 286 can sense a heart rate of a patient to establish a baseline heart rate. In one example, the processing apparatus 280 can thereafter determine, or confirm, that the patient complied with the request to initiate an activity by sensing and monitoring both the activity level and the heart rate of the patient during an activity event. After the patient has maintained an increased level of activity for a specified amount of time, the system 200 can employ the notification apparatus 282 to notify the patient to terminate exercise and begin resting. The sensing apparatus 286 can sense the heart rate at the activity termination and upon completion of a predetermined recovery period. The heart rate recovery can be determined by the processing apparatus 280 for the heart rate recovery event using the difference between, or delta of, the heart rate at the activity termination and the heart rate taken at completion of the predetermined recovery period.

In one example, if the processing apparatus 280 determines that a heart rate recovery event has not occurred in an extended period of time (e.g., 7 days), the patient may be notified, or prompted, by the notification apparatus 282 that heart rate recovery information is requested and to initiate a prescribed activity, or exercise regime. In one example, a notification may also be communicated by the communication apparatus 288 to a remote device, such as a monitoring device (e.g., computing device) at a physician's office.

Figure 6:
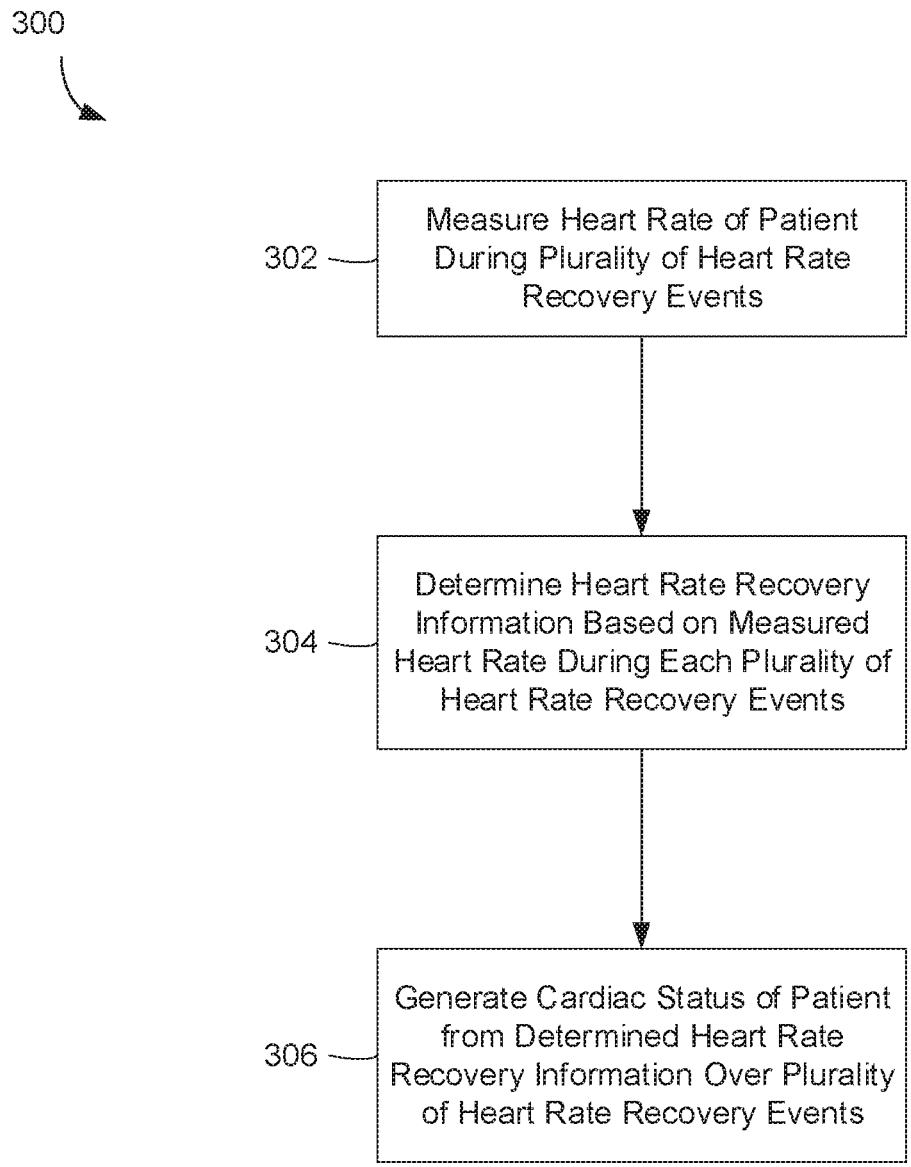
FIG. 6 illustrates a flow diagram of an example method of generating a cardiac status of a patient in accordance with aspects of the present disclosure.

FIG. 6 illustrates a flow diagram of an example method 300 of generating a cardiac status of a patient in accordance with aspects of the present disclosure. According to the illustrative example method 300, the heart rate of a patient can be measured, or sensed, during each of a plurality of heart rate recovery events at 302. Each of the plurality of heart rate recoveries, or heart rate recovery events, can be measured over a determined period of time immediately following an increase activity level, such as an exercise regime. The exercise regime can be specified or prescribed as occurring over a predetermined duration of time that is substantially the same for each of the plurality of heart rate recovery events of the patient. Alternatively, the specified or prescribed duration of time can be based on the heart health of the patient. For example, a patient with a relatively healthy heart may use a longer duration than a patient with a less healthy heart. One example exercise regime can include the patient stepping up onto a raised platform or step and then stepping down from the raised platform or step repeatedly and continuously at a prescribed rate over a duration of time, such as three minutes. In one example, the heart rate recovery of a patient with a relatively healthy may be 20 beats per minutes (bpm) while a patient experiencing Acute HF may be 5 bpm.

In some examples, heart rate recovery information of the patient can be determined based on the measured heart rate(s) during each of a plurality of heart rate recovery events at 304. In some examples, determining heart rate recovery information includes sensing, or measuring, a baseline heart rate (HR1) during a period of inactivity or low activity of the patient. This period of inactivity or low activity may be opportunistically identified by the device or proactively collected as a result of the device prompting the patient to cease activity. The patient then begins the exercise regime by increasing their activity level to a predetermined or threshold level for a predetermined or threshold active duration and a second heart rate (HR2) is sensed, or measured, at the end of the active duration. In other words, the activity resulting in the elevated heart rate may be performed resulting in the second heart rate. When the activity level of the patient is decreased to an inactive or low activity level, a third heart rate (HR3) may be sensed at the end of a predetermined or threshold recovery duration following the end of the activity. The heart rate recovery can be determined by subtracting HR3 from HR2. In other words, the change in heart rate from during activity to after a recovery period of time following the activity may be determined and used as heart rate recovery information.

The recovery period of time following the activity resulting in the elevated heart rate where heart rate recovery information may be determined may be between about 15 seconds to about 3 hours. In one or more embodiments, the recovery period of time may be greater than or equal to about 15 seconds, greater than or equal to about 25 seconds, greater than or equal to about 45 seconds, greater than or equal to about 1 minute, greater than or equal to about 2 minutes, greater than or equal to about 5 minutes, greater than or equal to about 15 minutes, greater than or equal to about 30 minutes, etc. and/or less than or equal to about 3 hours, less than or equal to about 2 hours, less than or equal to about 55 minutes, less than or equal to about 40 minutes, less than or equal to about 25 minutes, less than or equal to about 10 minutes, less than or equal to about 4 minutes, etc.

Over a time period encompassing a plurality of heart rate recovery events, for example, a cardiac status of the patient may be generated at 306 based on the heart rate recovery information determined during the plurality of heart rate recovery events.

The method 300 can include prompting the patient to initiate the activity (e.g., exercise regime) resulting in the elevated heart rate such that a heart rate recovery event can be monitored. Alternatively, the method can include determining whether the patient has initiated activity (e.g., exercise regime) resulting in the elevated heart rate such that during a heart rate recovery event can be monitored. For example, the intrinsic periods of activity (e.g., exercise) that meets or exceeds predetermined criteria, or thresholds, based on the activity level and heart rate elevation the patient can be automatically sensed.

A patient's compliance to a prescribed exercise regimen can factor into a determination of whether additional heart rate recovery events are desirable for generating a cardiac status of the patient. For example, the patient's compliance to a prescribed exercise regimen may result in the onset and offset of activity being less well defined or more abrupt than when the patient is prompted. Regardless, the device or system can determine that the patient is exercising based on sensed activity information such as heart rate, for example, and determine the heart rate recovery upon cessation of the exercise regime. In other words, sensing and monitoring the heart rate of the patient during the heart rate recovery events can be initiated based on a sensed decreased activity level of the patient indicating a ceasing of the elevated heart rate.

As discussed above with respect to FIG. 5B, at least one of the determined heart rate recovery information or the generated cardiac status can be communicated to an extra-corporeal, or external, device. In one example, a cardiac therapy delivered by an implantable medical device (e.g., pacemaker or subcutaneous drug delivery device) can be determined and/or adjusted based on the generated cardiac status. In one example, the generated cardiac status can be employed, or implemented, as a risk score for future heart failure events.

Figure 7:
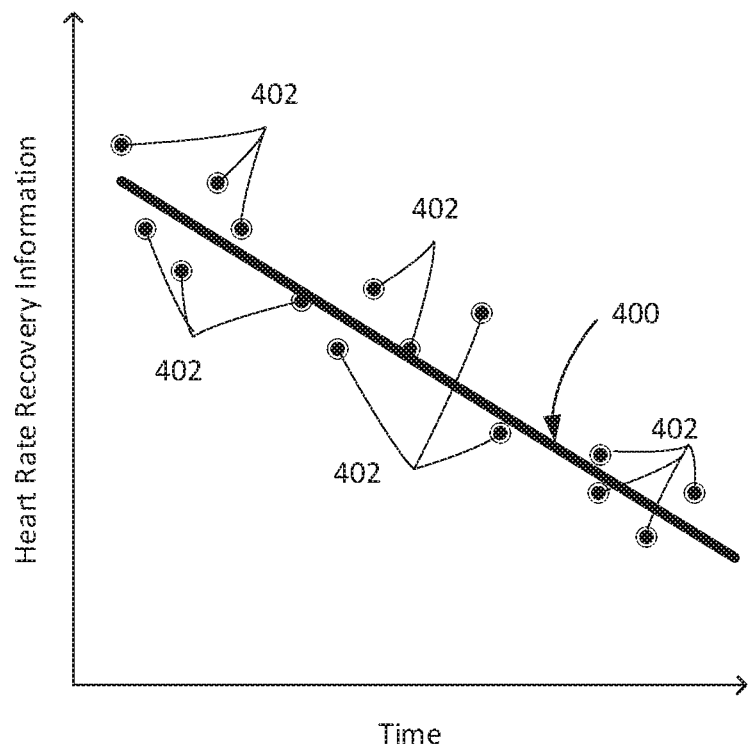
FIG. 7 is an example graphical illustration of a trend of heart rate recovery information for generating a cardiac status of a patient in accordance with aspects of the present disclosure.

FIG. 7 is an example graphical illustration of a trend of heart rate recovery information over time, which may be used to provide a cardiac status 400. A cardiac status, indicated by the line 400, can be generated using a plurality of heart rate recovery events 402 indicating a trend of heart rate recovery information generated from heart rate recovery events occurring over an extended period of time, such as days, weeks, or months, for example. In other words, a cardiac status of the patient can be based on the generated trend of heart rate recovery information. Each of the individual heart rate recovery events 402 are graphically indicated as a "●" in FIG. 7. More or less heart rate recovery events 402 can be used to generate the cardiac status 400 and the plurality of heart rate recovery events 402 included in FIG. 7 is for illustrative purposes only, as is the shape and slope of the cardiac status 400 generated from the plurality of heart rate recovery events 402. As indicated by the time axis, the heart rate recovery events 402 can be recorded chronologically over time to generate the cardiac status 400 of the patient. As graphically illustrated, the sensed information of each heart rate recovery taken over several heart rate recovery events 402 can be compiled to generate the cardiac status 400 indicative of the patient's heart health. The cardiac status 400 can be continuously or periodically generated with additional heart rate recovery events.

In one example, multiple heart rate recovery events 402 can be acquired in a given day (or other time period) with the intention of retaining the data from intrinsic exercise periods which are most similar (in terms of activity level, duration, max heart rate, etc.) in order to facilitate the most meaningful and accurate comparisons of heart rate recovery over time. This may allow for "personalization" of an exercise regimen for a given patient. For example, a healthy patient may be able to achieve a higher level of activity for a longer period of time compared to a less healthy patient. In one example, the illustrative devices, systems, or methods can monitor and record the patient's exercise patterns to generate a trend of the patient's exercise patterns over time and determine or develop tracking patterns related to times most useful to sense and monitor activity information. Such information can be gathered without the patient being at a physician's office.

The generated cardiac status described herein can be useful in projecting or anticipating future heart failure events or patient CHF prognosis and disease progress, for example. A cardiac status of a patient over a long period of time may assist a physician in diagnosis of a patient's cardiac condition and, in some examples, may assist in determining appropriate adjustments to cardiac therapy being delivered to the patient. For example, the generated cardiac status can be used to determine adjustments to pacing (e.g., A-V delay) delivered to the patient. An objective measure of long-term trends of patient activity and cardiac health, as generated with a cardiac status, may be useful in early or on-going identification and timely therapy to cardiac disease. For example, different patterns in recovery can be observed when COPD is worsening versus when HF is worsening in patients that have both, and thus, determining and generating a cardiac status of the patient can aid in differential diagnosis.

In response to the collected data and generated cardiac status, healthcare systems can respond in a variety of ways. Some healthcare systems may be able to generate health alerts based upon the cardiac status generated by the device 150 or system 200. One exemplary healthcare system may be described in U.S. Patent Application 2010/0030293 to Sarkar et al., which is incorporated by reference herein in its entirety, that is capable of generating alerts for a patient to seek medical treatment in response to cardiac status which is incorporated by reference in its entirety. For example, the device 150 or system 200 may detect worsening heart failure in a patient based on cardiac status, and, upon detecting worsening heart failure, an alert may be provided to the patient that enables the patient to seek medical attention before experiencing a heart failure event. In other examples, an alert can alternatively or additionally be provided to a physician's office such as via the internet and a computing device at the physician's office.

EXEMPLARY EMBODIMENTS

Embodiment 1. A method comprising:
measuring a heart rate of a patient during a plurality of heart rate recovery events, wherein each of the plurality of heart rate recovery events comprises a duration of time after an activity resulting in an elevated heart rate;
determining heart rate recovery information based on the measured heart rate during each of the plurality of heart rate recovery events;
generating a trend of heart rate recovery information from the determined heart rate recovery information over the plurality of heart rate recovery events over a period of time;
generating a cardiac status of the heart failure patient based on the generated trend of heart rate recovery information; and
detecting worsening heart failure in the heart failure patient based on the cardiac status.

Embodiment 2. The method as set forth in embodiment 1, wherein the duration of time is substantially the same for each of the plurality of heart rate recovery events of the heart failure patient.

Embodiment 3. The method as set forth in any one of embodiments 1-2, wherein the duration of time is based on the heart health of the heart failure patient.

Embodiment 4. The method as set forth in any one of embodiments 1-3, further comprising:
prompting the heart failure patient to initiate the activity resulting in the elevated heart rate.

Embodiment 5. The method as set forth in any one of embodiments 1-4, further comprising:
sensing an activity level of the heart failure patient,
wherein measuring the heart rate of the heart failure patient during a heart rate recovery event is initiated based on a sensed decrease in the activity level of the heart failure patient.

Embodiment 6. The method as set forth in any one of embodiments 1-5, further comprising:
communicating at least one of the determined heart rate recovery information and the generated cardiac status to an extracorporeal device.

Embodiment 7. The method as set forth in any one of embodiments 1-6, further comprising:
initiating a cardiac therapy to the heart failure patient to be delivered by an implantable medical device based on the generated cardiac status.

Embodiment 8. The method as set forth in any one of embodiments 1-7, further comprising issuing an alert to seek medical attention to the heart failure patient in response to detecting worsening.

Embodiment 9. A device comprising:
a sensor apparatus comprising a heart rate sensor to sense a heart rate of a heart failure patient; and
a processing apparatus operably coupled to the sensor apparatus and comprising processing circuitry configured to:
monitor a heart rate of the heart failure patient using the heart rate sensor during a plurality of heart rate recovery events, wherein each of the plurality of heart rate recovery events comprises a duration of time after an activity resulting in an elevated heart rate, determine heart rate recovery information based on the measured heart rate during each of the plurality of heart rate recovery events, and
generate a trend of heart rate recovery information from the determined heart rate recovery information over the plurality of heart rate recovery events over a period of time;
generate a cardiac status of the heart failure patient based on the generated trend of heart rate recovery information; and
detect worsening heart failure in the heart failure patient based on the cardiac status.

Embodiment 10. The device as set forth in embodiment 9, further comprising:
a notification apparatus to notify the heart failure patient to initiate an activity resulting the elevated heart rate.

Embodiment 11. The device as set forth in embodiment 10, wherein the processing circuitry is further configured to issue, using the notification apparatus, an alert to seek medical attention to the heart failure patient in response to detecting worsening.

Embodiment 12. The device as set forth in any one of embodiments 9-11, wherein the processing apparatus further comprises communication circuitry configured to communicate at least one of the heart rate recovery information and cardiac status to another external device.

Embodiment 13. The device as set forth in any one of embodiments 9-12, wherein the sensing apparatus further comprises an activity level sensor to sense an activity level of the heart failure patient, and wherein the processing circuitry is further configured to sense an activity level of the patient using the activity level sensor to determine a termination of the activity based on a decrease in a sensed activity level.

Embodiment 14. The device as set forth in any one of embodiments 9-13, wherein the processing circuitry is further configured to determine a therapy to be delivered to the heart failure patient based on the generated cardiac status.

Embodiment 15. The device as set forth in any one of embodiments 9-14, wherein the processing circuitry is further configured to determine a pacing rate of a cardiac therapy to be delivered by a pacing device to a heart of the heart failure patient based on the generated cardiac status.

Embodiment 16. The device as set forth in any one of embodiments 9-15, further comprising:
at least one pacing electrode; and
therapy delivery circuitry operably coupled to the at least one electrode to deliver cardiac therapy to a heart of the heart failure patient based the generated cardiac status.

Embodiment 17. A system comprising:
a sensor apparatus comprising a heart rate sensor to sense a heart rate of a heart failure patient;
a processing apparatus operably coupled to the sensor apparatus and comprising processing circuitry configured to:
measure a heart rate of the heart failure patient during a plurality of heart rate recovery events, wherein each of the plurality of heart rate recovery events comprises a duration of time after an activity resulting in an elevated heart rate, determine heart rate recovery information based on the measured heart rate during each of the plurality of heart rate recovery events, and generate a trend of heart rate recovery information over a period of time;
detect worsening heart failure in the heart failure patient based on the generated trend of heart rate recovery information; and
a notification apparatus to notify the heart failure patient to initiate an activity resulting in the elevated heart rate Embodiment 18. The system as set forth in embodiment 17, wherein the processing apparatus further comprises communication circuitry configured to communicate at least one of the heart rate recovery information and the generated trend of heart rate recovery information to another external device.

Embodiment 19. The system as set forth in any one of embodiments 17-18, wherein the sensing apparatus further comprises an activity level sensor to sense an activity level of the heart failure patient, and wherein the processing circuitry is further configured to sense an activity level of the heart failure patient using the activity level sensor to determine a termination of the activity based on a decrease in a sensed activity level.

Embodiment 20. The system as set forth in any one of embodiments 17-19, wherein the processing circuitry is further configured to determine a pacing rate of a cardiac therapy to be delivered by a pacing device to a heart of the heart failure patient based on the generated trend of heart rate recovery information.

Embodiment 21. A method comprising:
measuring a perturbation effect of a patient during a plurality of perturbation recovery events, wherein each of the plurality of perturbation recovery events comprises a duration of time after the patient is perturbed;
determining perturbation recovery information based on the measured perturbation effect during each of the plurality of perturbation recovery events; and
generating a cardiac status of the patient from the determined perturbation recovery information over the plurality of perturbation recovery events.

Embodiment 22. The method as set forth in embodiment 21, further comprising: generating a trend of heart rate recovery information over a period of time, wherein the generated cardiac status of the patient is based on the generated trend of heart rate recovery information.

Embodiment 23. The method as set forth in embodiment 21, wherein the patient perturbance comprises a syncopal event.

Embodiment 24. The method as set forth in embodiment 21, wherein the patient perturbance comprises a premature depolarization.

Embodiment 25. The method as set forth in embodiment 21, wherein the patient perturbance comprises an infection.

Embodiment 26. A device comprising:
a sensor apparatus comprising a heart rate sensor to sense a heart rate of a patient; and
a processing apparatus operably coupled to the sensor apparatus and comprising processing circuitry configured to:
measure a perturbation effect of a patient during a plurality of perturbation recovery events, wherein each of the plurality of perturbation recovery events comprises a duration of time after the patient is perturbed,
determine perturbation recovery information based on the measured perturbation effect during each of the plurality of perturbation recovery events, and
generate a cardiac status of the patient from the determined perturbation recovery information over the plurality of perturbation recovery events.

Embodiment 26. The device as set forth in embodiment 26, wherein the processing apparatus further comprises communication circuitry configured to communicate at least one of the heart rate recovery information and cardiac status to another external device.

Embodiment 27. The device as set forth in embodiment 26, wherein the patient perturbance comprises a syncopal event.

Embodiment 28. The device as set forth in embodiment 26, wherein the patient perturbance comprises a premature depolarization.

Embodiment 29. The device as set forth in embodiment 26, wherein the patient perturbance comprises an infection.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Although the present disclosure has been described with reference to preferred embodiments, workers skilled in the art will recognize that changes can be made in form and detail without departing from the spirit and scope of the present disclosure.

What is claimed:

1. A method comprising:
measuring a heart rate of a heart failure patient during a plurality of heart rate recovery events, wherein each of the plurality of heart rate recovery events comprises a duration of time after an activity resulting in an elevated heart rate;
determining heart rate recovery information based on the measured heart rate during each of the plurality of heart rate recovery events, wherein the heart rate recovery information for each of the plurality of heart rate recovery events comprises a difference between the elevated heart rate and a recovery heart rate measured at the completion of the heart rate recovery event;
generating a trend of heart rate recovery information from the determined heart rate recovery information over the plurality of heart rate recovery events over a period of time;
generating a cardiac status of the heart failure patient based on the generated trend of heart rate recovery information; and
detecting worsening heart failure in the heart failure patient in response to the cardiac status being indicative of a downward trend of the difference between the elevated heart rate and the recovery heart rate over the plurality of heart rate recovery events.

2. The method of claim 1, wherein the duration of time is substantially the same for each of the plurality of heart rate recovery events of the heart failure patient.

3. The method of claim 1, wherein the duration of time is based on the heart health of the heart failure patient.

4. The method of claim 1, further comprising:
prompting the heart failure patient to initiate the activity resulting in the elevated heart rate.

5. The method of claim 1, further comprising:
sensing an activity level of the heart failure patient,
wherein measuring the heart rate of the patient during a heart rate recovery event is initiated based on a sensed decrease in the activity level of the heart failure patient.

6. The method of claim 1, further comprising:
communicating at least one of the determined heart rate recovery information and the generated cardiac status to an extracorporeal device.

7. The method of claim 1, further comprising:
initiating a cardiac therapy to the heart failure patient to be delivered by an implantable medical device based on the generated cardiac status.

8. The method of claim 1, further comprising issuing an alert to seek medical attention to the heart failure patient in response to detecting worsening.

9. A device comprising:
a sensor apparatus comprising a heart rate sensor to sense a heart rate of a heart failure patient; and
a processing apparatus operably coupled to the sensor apparatus and comprising processing circuitry configured to:
monitor a heart rate of the heart failure patient using the heart rate sensor during a plurality of heart rate recovery events, wherein each of the plurality of heart rate recovery events comprises a duration of time after an activity resulting in an elevated heart rate;
determine heart rate recovery information based on the monitored heart rate during each of the plurality of heart rate recovery events, wherein the heart rate recovery information for each of the plurality of heart rate recovery events comprises a difference between the elevated heart rate and a recovery heart rate measured at the completion of the heart rate recovery event;
generate a trend of heart rate recovery information from the determined heart rate recovery information over the plurality of heart rate recovery events over a period of time;
generate a cardiac status of the heart failure patient based on the generated trend of heart rate recovery information; and
detect worsening heart failure in the heart failure patient in response to the cardiac status being indicative of a downward trend of the difference between the elevated heart rate and the recovery heart rate over the plurality of heart rate recovery events.

10. The device of claim 9, further comprising:
a notification apparatus to notify the heart failure patient to initiate an activity resulting in the elevated heart rate.

11. The device of claim 10, wherein the processing circuitry is further configured to issue, using the notification apparatus, an alert to seek medical attention to the heart failure patient in response to detecting worsening.

12. The device of claim 9, wherein the processing apparatus further comprises communication circuitry configured to communicate at least one of the heart rate recovery information and cardiac status to another external device.

13. The device of claim 9, wherein the sensing apparatus further comprises an activity level sensor to sense an activity level of the heart failure patient, and wherein the processing circuitry is further configured to sense an activity level of the heart failure patient using the activity level sensor to determine a termination of the activity based on a decrease in a sensed activity level.

14. The device of claim 9, wherein the processing circuitry is further configured to determine a therapy to be delivered to the heart failure patient based on the generated cardiac status.

15. The device of claim 9, wherein the processing circuitry is further configured to determine a pacing rate of a cardiac therapy to be delivered by a pacing device to a heart of the heart failure patient based on the generated cardiac status.

16. The device of claim 9, further comprising:
at least one pacing electrode; and
therapy delivery circuitry operably coupled to the at least one electrode to deliver cardiac therapy to a heart of the heart failure patient based the generated cardiac status.

17. A system comprising:
a sensor apparatus comprising a heart rate sensor to sense a heart rate of a heart failure patient;
a processing apparatus operably coupled to the sensor apparatus and comprising processing circuitry configured to:
measure a heart rate of the heart failure patient during a plurality of heart rate recovery events, wherein each of the plurality of heart rate recovery events comprises a duration of time after an activity resulting in an elevated heart rate;
determine heart rate recovery information based on the measured heart rate during each of the plurality of heart rate recovery events, wherein the heart rate recovery information for each of the plurality of heart rate recovery events comprises a difference between the elevated heart rate and a recovery heart rate measured at the completion of the heart rate recovery event;
generate a trend of heart rate recovery information over a period of time; and
detect worsening heart failure in the heart failure patient in response to the generated trend of heart rate recovery information being indicative of a downward trend of the difference between the elevated heart rate and the recovery heart rate over the plurality of heart rate recovery events; and
a notification apparatus to notify the heart failure patient to initiate an activity resulting in the elevated heart rate.

18. The system of claim 17, wherein the processing apparatus further comprises communication circuitry configured to communicate at least one of the heart rate recovery information and the generated trend of heart rate recovery information to another external device.

19. The system of claim 17, wherein the sensing apparatus further comprises an activity level sensor to sense an activity level of the heart failure patient, and wherein the processing circuitry is further configured to sense an activity level of the heart failure patient using the activity level sensor to determine a termination of the activity based on a decrease in a sensed activity level.

20. The system of claim 17, wherein the processing circuitry is further configured to determine a pacing rate of a cardiac therapy to be delivered by a pacing device to a heart of the heart failure patient based on the generated trend of heart rate recovery information.

* * * * *